US00PP37302P2

(12) United States Plant Patent
de Vos

(10) Patent No.: US PP37,302 P2
(45) Date of Patent: Mar. 3, 2026

(54) ***HYDRANGEA* PLANT NAMED 'HORE9306'**

(50) Latin Name: *Hydrangea macrophylla*
Varietal Denomination: HORE9306

(71) Applicant: KWEKERIJ LENDERT de VOS B.V., Reeuwijk (NL)

(72) Inventor: Lendert de Vos, Reeuwijk (NL)

(73) Assignee: KWEKERIJ LENDERT de VOS B.V., Reeuwijk (NL)

( * ) Notice: Subject to any disclaimer, the term of this patent is extended or adjusted under 35 U.S.C. 154(b) by 0 days.

(21) Appl. No.: 19/030,116

(22) Filed: Jan. 17, 2025

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hydrangea* plant named 'HORE9306', characterized by its relatively compact, upright to broadly spreading plant habit; relatively moderately vigorous growth habit; freely branching habit; strong and sturdy stems; freely flowering habit; panicles with double-type sterile flowers that are pale purple in color; and good postproduction longevity.

2 Drawing Sheets

Figure 1:
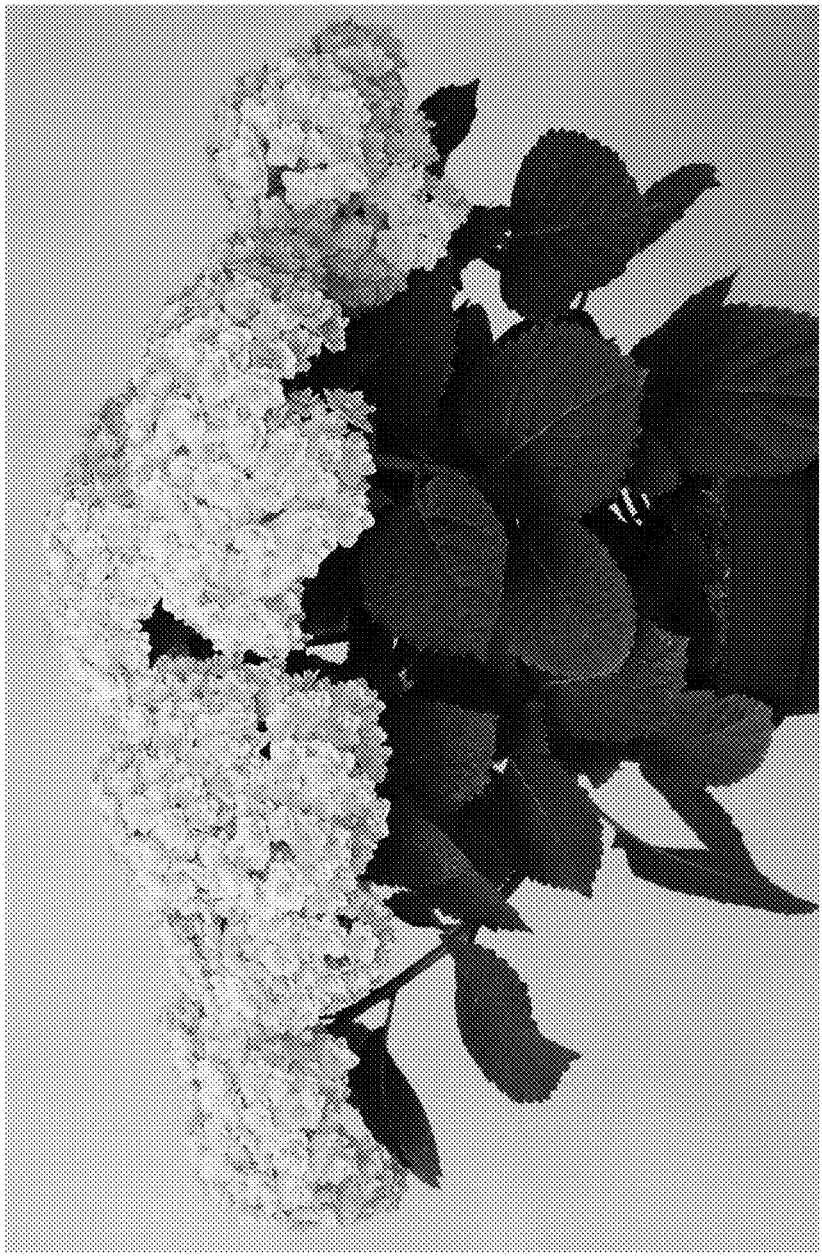

Botanical designation: *Hydrangea macrophylla.*
Cultivar denomination: 'HORE9306'.

CROSS-REFERENCED TO CLOSELY-RELATED APPLICATIONS

A United Kingdom Plant Breeder's Rights application for this plant was filed by the Applicant/Assignee of the instant application, Kwekerij Lendert de Vos of Reeuwijk, The Netherlands on Aug. 20, 2024, application number 23/883, and published on Sep. 1, 2024. Foreign priority is not claimed to this United Kingdom Plant Breeder's Rights application.

A European Community Plant Breeder's Rights application for this plant was filed by the Applicant/Assignee of the instant application, Kwekerij Lendert de Vos of Reeuwijk, The Netherlands on Sep. 24, 2024, application number 2024/2228, and published on Dec. 15, 2024. Foreign priority is not claimed to this European Plant Breeder's Rights application.

BACKGROUND OF THE INVENTION

The present invention relates to a new and distinct cultivar of *Hydrangea* plant, botanically known as *Hydrangea macrophylla*, commercially referred to as a Bigleaf Hydrangea and hereinafter referred to by the name 'HORE9306'.

The new *Hydrangea* plant is a product of a planned breeding program conducted by the Inventor in Reeuwijk, The Netherlands. The objective of the breeding program is to create new compact and strong *Hydrangea* plants with attractive inflorescences and good postproduction longevity.

The new *Hydrangea* plant originated from a cross-pollination in August 2017 of a proprietary selection of *Hydrangea* macrophylla identified as code number 16-20161-02, not patented, as the female, or seed, parent with a proprietary of Hydrangea macrophylla identified as code number 16-20143-03, not patented, as the male, or pollen, parent. The new *Hydrangea* plant was discovered and selected as a single flowering plant from within the progeny of the stated cross-pollination in a controlled greenhouse environment in Reeuwijk, The Netherlands in August 2019.

Asexual reproduction of the new *Hydrangea* plant by terminal vegetative cuttings since August 2019 in a controlled greenhouse environment in Reeuwijk, The Netherlands has shown that the unique features of this new *Hydrangea* plant are stable and reproduced true to type in successive generations of asexual reproduction.

SUMMARY OF THE NEW PLANT

Plants of the new *Hydrangea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HORE9306'. These characteristics in combination distinguish 'HORE9306' as a new and distinct *Hydrangea* plant:

1. Relatively compact, upright to broadly spreading plant habit.
2. Relatively moderately vigorous growth habit.
3. Freely branching habit.
4. Strong and sturdy stems.
5. Freely flowering habit.
6. Panicles with double-type sterile flowers that are pale purple in color.
7. Good postproduction longevity.

Plants of the new *Hydrangea* can be compared to plants of the female parent selection. Plants of the new *Hydrangea* differ primarily from plants of the female parent selection in the following characteristics:

1. Plants of the new *Hydrangea* are more compact than plants of the female parent selection.
2. Plants of the new *Hydrangea* have double-type sterile flowers whereas plants of the female parent selection have single-type sterile flowers.
3. Flowers of plants of the new *Hydrangea* are sterile whereas flowers of plants of the female parent selection are fertile.

Plants of the new *Hydrangea* can be compared to plants of the male parent selection. Plants of the new *Hydrangea* differ primarily from plants of the male parent selection in the following characteristics:

1. Plants of the new *Hydrangea* are more compact than plants of the male parent selection.
2. Plants of the new *Hydrangea* have double-type sterile flowers whereas plants of the male parent selection have single-type sterile flowers.
3. Flowers of plants of the new *Hydrangea* are sterile whereas flowers of plants of the male parent selection are fertile.

Plants of the new *Hydrangea* can be compared to plants of *Hydrangea macrophylla* 'HORE9311', disclosed in U.S. Plant patent application Ser. No. 19/030,145. In side-by-side comparisons, plants of the new *Hydrangea* differ primarily from plants of 'HORE9311' in sterile flower color as plants of the new *Hydrangea* have pale purple-colored sterile flowers whereas plants of 'HORE9311' have greenish white to white-colored sterile flowers.

Plants of the new *Hydrangea* can be compared to plants of *Hydrangea macrophylla* 'Youmefive', not patented. In side-by-side comparisons, plants of the new *Hydrangea* differ primarily from plants of 'Youmefive' in the following characteristics:

1. Plants of the new *Hydrangea* are more freely branching than plants of 'Youmefive'.
2. Inflorescences of plants of the new *Hydrangea* are more uniformly rounded than inflorescences of plants of 'Youmefive'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HORE9306' grown in a container.

Figure 2:
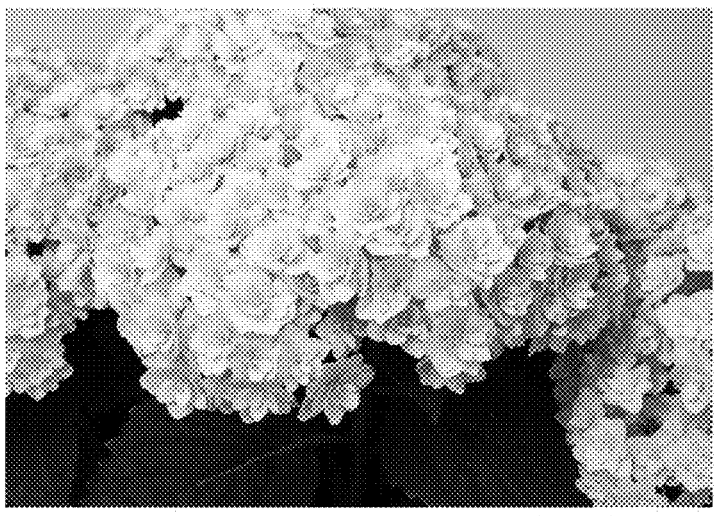

The photograph at the top of the second sheet (FIG. 2) is a close-up view of typical inflorescences of 'HORE9306'.

Figure 3:
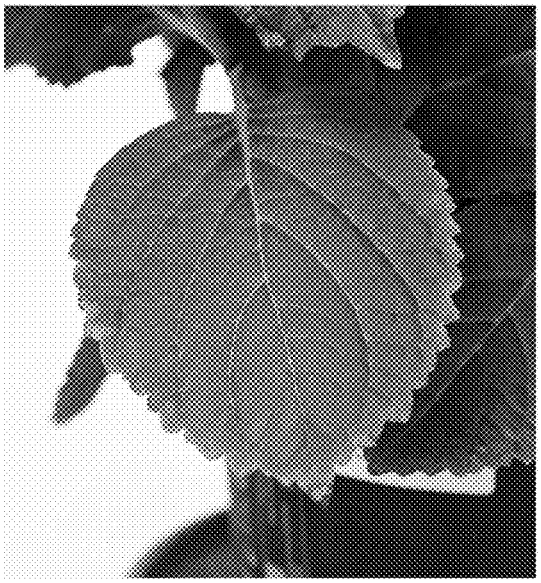

The photograph at the bottom of the second sheet (FIG. 3) is a close-up view of typical leaves of 'HORE9306'.

DETAILED BOTANICAL DESCRIPTION

Plants used in the aforementioned photographs and in the following description were grown during the summer in 21-cm containers in a glass-covered greenhouse in Reeuwijk, The Netherlands and under cultural practices typical of commercial *Hydrangea* production. During the production of the plants, day temperatures ranged from 20° C. to 35° C. and night temperatures ranged from 10° C. to 22° C. Plants of the new *Hydrangea* were pinched one time and were 18 months old when the photographs and description were taken. In the following description, color references are made to The Royal Horticultural Society Colour Chart, Sixth Edition, except where general terms of ordinary dictionary significance are used. The new *Hydrangea* plant is not typically treated with aluminum sulfate to "blue" the flower color.

Botanical description:

*Hydrangea macrophylla* 'HORE9306'.

Parentage:

*Female, or seed, patent*—Proprietary selection of *Hydrangea macrophylla* identified as code number 16-20161-02, not patented.

*Male, or pollen, patent*—Proprietary selection of *Hydrangea macrophylla* identified as code number 16-20143-03, not patented.

Propagation:

*Type cutting*—By vegetative terminal cuttings.

*Time to initiate roots, summer*—About 16 days at temperatures ranging from 20° C. to 30° C.

*Time to produce a rooted young plant, summer*—About four months at temperatures ranging from 20° C. to 3° C.

*Root description*—Medium in thickness; fibrous; typically light brown in color, actual color of the roots is dependent on substrate composition, water quality, fertilizer type and formulation, substrate temperature and physiological age of roots.

*Rooting habit*—Freely branching; dense.

Plant description:

*Plant and growth habit*—Relatively compact; upright to broadly outwardly spreading and mounding plant habit; overall shape, flattened globular; strong and sturdy stems; relatively moderately vigorous growth habit and moderate growth rate; about six months from propagation are required to produce small finished plants.

*Plant height*—About 36.5 cm.

*Plant diameter or area of spread*—About 57.5 cm.

Lateral branch description:

*Branching habit*—Freely branching habit with about twelve lateral branches developing per plant; pinching is not required, but will enhance lateral branch development.

*Length*—About 19 cm.

*Diameter*—About 6.5 mm.

*Internode length*—About 4.6 cm.

*Strength*—Strong, sturdy.

*Aspect*—Erect to about 55° from vertical.

*Texture*—Smooth, glabrous; becoming woody with subsequent development.

*Color, developing*—Close to 144A.

*Color, fully developed*—Close to 144A; at the nodes, slightly tinged with close to 183B; when woody, close to 199A to 199C and N199C.

*Lenticels*—Density: Medium density. Length: About 2 mm. Diameter: About 0.5 mm. Color: Close to a blend of N186C and 200A.

Leaf description:

*Arrangement*—Opposite, simple.

*Length*—About 11.2 cm.

*Width*—About 9.1 cm.

*Shape*—Broadly ovate.

*Apex*—Apiculate.

*Base*—Rounded to truncate.

*Margin*—Coarsely dentate-serrate.

*Texture and luster, upper and lower surfaces*—Smooth, glabrous; slightly rugose; slightly glossy.

*Venation pattern*—Pinnate.

*Color*—Developing leaves, upper surface: Close to NN137A. Developing leaves, lower surface: Close to 146A. Fully developed leaves, upper surface: Close to a blend of 147A and N189A; venation, close to 146D. Fully developed leaves, lower surface: Close to NN137D; venation, close to 146D.

*Petioles*—Length: About 2.3 cm. Diameter: About 3.5 mm. Texture and luster, upper and lower surfaces: Smooth, glabrous; slightly glossy. Color, upper surface: Close to 146D. Color, lower surface: Close to 144A.

Flower description:

*Flower type and habit*—Rotate double-type sterile flowers arranged on terminal hemispherical panicles; panicles flattened globular in overall shape; sterile flowers face upright to outwardly; fertile flower bud development has been observed on plants of the new *Hydrangea*, however, to date, fertile flower buds have not been observed to further develop into open flowers; fertile flower buds mostly upright.

*Fragrance*—None detected.

*Natural flowering season*—Plants flower continuously for about three months; in garden in The Netherlands, plants flower from late spring into the late summer.

*Flower longevity*—Good postproduction longevity; sterile flowers maintain good substance for about six weeks on the plant, sterile flowers persistent.

*Quantity of flowers*—Freely flowering habit; about 450 sterile flowers per panicle and about 150 fertile flowers buds per panicle.

*Panicle height*—About 10.5 cm.

*Panicle diameter*—About 19.9 cm.

*Panicle peduncles*—Length: About 9.2 cm. Diameter: About 4 mm. Strength: Strong. Aspect: Primary peduncles, mostly erect; lateral peduncles, about 30° from primary peduncle axis. Texture and luster: Moderately to densely pubescent; matte. Color: Close to 146B and 146C; at the nodes, slightly tinged with close to 182B. Lenticels: Density: Sparse to medium density. Length: About 1 mm. Diameter: About 0.5 mm. Color: Close to 200C.

*Sterile flower buds*—Length: About 8 mm. Diameter: About 1.3 cm. Shape: Cup-shaped. Color: Close to 85D; towards the base, close to 77D.

*Fertile flower buds*—Length: About 1 mm. Diameter: About 1 mm. Shape: Globular. Color: Close to 144A.

*Sterile flower diameter*—About 2.5 cm.

*Sterile flower depth (height)*—About 9 mm.

*Petals, sterile flowers*—To date, petal development has not been observed on sterile flowers of plants of the new *Hydrangea*.

*Sepals, sterile flowers*—Quantity and arrangement: About 18 in multiple whorls. Length: About 1.3 mm. Width: About 1 cm. Shape: Broadly ovate; mostly flat to slightly concave. Apex: Minutely retuse. Base: Broadly attenuate. Margin: Entire. Texture and luster, upper and lower surfaces: Smooth, glabrous; matte. Color: When opening, upper and lower surfaces: Close to a blend of 85C and 85D; towards the base, close to N75D. Fully opened, upper and lower surfaces: Close to 76C; at the base, tinged with close to N75D; with subsequent development, color becoming closer to N155B and at the base, tinged with close to 76B and 76C.

*Pedicels, sterile flowers*—Length: About 2 cm. Diameter: About 1 mm. Strength: Moderately strong. Aspect: About 40° from main peduncle axis. Texture and luster: Moderately to densely pubescent; matte. Color: Close to 75B to 75C.

*Reproductive organs, sterile flowers*—Stamens: To date, stamen development has not been observed on plants of the new *Hydrangea*. Pistils: Pistil quantity per flower: Typically five. Pistil length: About 1 mm. Stigma shape: Club-shaped. Stigma color: Close to 145D. Style length: About 0.75 mm. Style color: Close to 145B. Ovary color: Close to 145B.

*Fruits and seeds*—To date, fruit and seed development has not been observed on plants of the new *Hydrangea*.

Pathogen & pest resistance:

Plants of the new Hydrangea have not been observed to be resistant to pathogens and pests common to *Hydrangea* plants.

Temperature tolerance:

Plants of the new *Hydrangea* have been shown to be suitable for USDA Hardiness Zones 5 through 9.

It is claimed:

1. A new and distinct *Hydrangea* plant named 'HORE9306' as herein illustrated and described.

* * * * *